United States Patent [19]

Gillberg-LaForce et al.

[11] Patent Number: 5,700,531
[45] Date of Patent: Dec. 23, 1997

[54] PULL-ACTIVATED CONTAINER

[75] Inventors: Gunilla Elsa Gillberg-LaForce, Roswell; Kevin George Hetzler, Alpharetta; Rob Lee Jacobs, Woodstock, all of Ga.

[73] Assignee: Kimberly-Clark Worldwide, Inc., Neenah, Wis.

[21] Appl. No.: 559,902

[22] Filed: Nov. 17, 1995

[51] Int. Cl.⁶ .................... B29D 22/00; B32B 27/00
[52] U.S. Cl. ............... 428/36.1; 442/398; 442/401
[58] Field of Search ................ 428/36.1, 284, 428/286; 442/398, 401

[56] References Cited

U.S. PATENT DOCUMENTS

| | | | |
|---|---|---|---|
| Re. 33,646 | 7/1991 | Klemm et al. | 252/90 |
| D. 356,688 | 3/1995 | Uitenbroek et al. | D5/52 |
| 2,389,736 | 11/1945 | Muise | 152/91 |
| 3,016,599 | 1/1962 | Perry, Jr. | 28/78 |
| 3,341,394 | 9/1967 | Kinney | 161/72 |
| 3,485,562 | 12/1969 | Hidden et al. | 401/134 |
| 3,630,800 | 12/1971 | Nash et al. | 156/229 |
| 3,655,862 | 4/1972 | Dorschner et al. | 264/290 |
| 3,692,618 | 9/1972 | Dorschner et al. | 171/62 |
| 3,704,198 | 11/1972 | Prentice | 161/148 |
| 3,705,068 | 12/1972 | Dobo et al. | 156/441 |
| 3,755,527 | 8/1973 | Keller et al. | 264/210 |
| 3,801,404 | 4/1974 | Druin et al. | 156/229 |
| 3,802,817 | 4/1974 | Matsuki et al. | 425/66 |
| 3,849,241 | 11/1974 | Butin et al. | 161/169 |
| 3,853,651 | 12/1974 | Porte | 156/73.6 |
| 3,855,046 | 12/1974 | Hansen et al. | 161/150 |
| 3,978,185 | 8/1976 | Butin et al. | 264/93 |
| 4,064,605 | 12/1977 | Akiyama et al. | 28/103 |
| 4,091,140 | 5/1978 | Harmon | 428/288 |
| 4,100,319 | 7/1978 | Schwartz | 428/171 |
| 4,100,324 | 7/1978 | Anderson et al. | 428/288 |
| 4,118,531 | 10/1978 | Hauser | 428/224 |
| 4,330,220 | 5/1982 | Schaar et al. | 401/134 |
| 4,340,563 | 7/1982 | Appel et al. | 264/518 |
| 4,395,261 | 7/1983 | Lutz | 8/111 |
| 4,405,297 | 9/1983 | Appel et al. | 425/72 |
| 4,430,013 | 2/1984 | Kaufman | 401/132 |
| 4,434,204 | 2/1984 | Hartman et al. | 428/198 |
| 4,448,704 | 5/1984 | Barby et al. | 252/91 |
| 4,472,328 | 9/1984 | Sugimoto et al. | 264/41 |
| 4,493,868 | 1/1985 | Meitner | 428/171 |
| 4,515,703 | 5/1985 | Haq | 252/92 |
| 4,519,909 | 5/1985 | Castro | 210/500.2 |
| 4,627,811 | 12/1986 | Greiser et al. | 425/72 |
| 4,644,045 | 2/1987 | Fowells | 526/348 |
| 4,663,220 | 5/1987 | Wisneski et al. | 428/221 |
| 4,795,665 | 1/1989 | Lancaster et al. | 428/34.2 |
| 4,820,435 | 4/1989 | Zafiroglu | 252/90 |
| 4,839,076 | 6/1989 | Willman et al. | 252/90 |
| 4,891,389 | 1/1990 | Graiver et al. | 521/64 |
| 4,904,524 | 2/1990 | Yoh | 428/311.3 |
| 4,915,301 | 4/1990 | Munteanu | 239/45 |
| 4,917,301 | 4/1990 | Munteanu | 239/43 |
| 4,925,327 | 5/1990 | Wirt | 401/205 |
| 4,948,047 | 8/1990 | Zembrodt | 239/34 |
| 5,158,810 | 10/1992 | Oishi et al. | 428/35.4 |
| 5,171,308 | 12/1992 | Gallagher et al. | 604/372 |
| 5,182,162 | 1/1993 | Andrusko | 428/219 |
| 5,238,760 | 8/1993 | Takahashi et al. | 429/194 |
| 5,310,587 | 5/1994 | Akahori et al. | 428/35.2 |
| 5,470,624 | 11/1995 | Oreglia et al. | 428/36.1 |

FOREIGN PATENT DOCUMENTS

| | | |
|---|---|---|
| 0 604 731 | 7/1994 | European Pat. Off. |
| 91/10375 | 7/1991 | WIPO |

OTHER PUBLICATIONS

V.A. Wente, "Superfine Thermoplastic Fibers", *Industrial & Engineering Chem.*, V. 48, N. 8, pp. 1342–1346, 1956.

V.A. Wente, "Manufacture of Superfine Organic Fibers", *Navy Research Lab.*, Washington, D.C., NRL Rpt. 4364 (111437), May 25, 1954. U.S. Dept. of Commerce, Office of Technical Services.

R.R. Butin, et al., "Melt Blowing—A One Step Web Process for New Nonwoven Products", *Journal of the Tech. Assoc. of The Pulp and Paper Industry*, V. 56, N.4, pp. 74–77, 1973.

B.S. Sprague, "Relationship of Structure and Morphology to Properties of Hard Elastic Fibers and Films", *Journal of Macromol. Sci.–Phys.*, B8, (1–2), 157–187, (1973).

S.L. Cannon, et al., "Hard–Elastic Fibers (A Review of A Novel State for Crystalline Polymers)", *J. Polymer Science: Macromolecular Reviews*, vol. 11, 209–275, (1976).

*Encyclopedia of Polymer Science And Engineering*, vol. 7, John Wiley & Sons, Inc., pp. 73–91.

*Encyclopedia of Chemical Technology*, 4th Ed., vol. 10, John Wiley & Sons, Inc., pp. 761–783.

*Polypropylene Structure, Blends And Composites*, vol. 2, Chapman & Hall, pp. 17–23.

*Primary Examiner*—Helen Lee
*Attorney, Agent, or Firm*—William E. Maycock

[57] ABSTRACT

A pull-activated container adapted to hold a fluid, volatile solid, or absorbent for a fluid wherein at least a portion of the container includes a laminate which, in turn, includes a first layer, a second layer, a third layer, and a grasping means. The first layer is a fibrous sheet, the second layer is a film having a first side and a second side, and the third layer is a porous fibrous sheet. The third layer is inside the container. The first layer is bonded to the first side of the second layer and has a first bonding strength and the third layer is bonded to the second side of the second layer and has a second bonding strength. For example, the first bonding strength may be greater than the second bonding strength to an extent sufficient to permit selectively removing the first and second layers from the third layer without tearing the third layer. The grasping means is affixed to the first layer and has a third bonding strength which is greater than the second bonding strength. If desired, a portion of the first layer may be defined by lines of weakness sufficient to aid in removing such portion at least partially from the third layer. Desirably, the grasping means will be attached to the portion of the first layer which is defined by lines of weakness.

12 Claims, No Drawings

PULL-ACTIVATED CONTAINER

BACKGROUND OF THE INVENTION

The present invention relates to a container, such as a dispensing container for a fluid, e.g., a liquid or volatile material.

Numerous devices for dispensing a material are known. Such devices range from a simple cloth to complex packages or containers for the controlled release of the material to be dispensed. Moreover, the material to be dispensed can be a solid, liquid, or gas.

Dispensing cloths include wet wipes and cloths impregnated with oil, lotion, or soap, all of which are concerned with skin care, particularly for infants. Dispensing cloths also have been employed for cleaning hard surfaces. Devices functionally equivalent to dispensing cloths utilize a microporous polymer for the dispensing of a wide variety of liquids, such as lubricants, surfactants, slip agents, moth repellents, pesticides, plasticizers, medicinals, fuel additives, polishing agents, stabilizers, insect and animal repellents, fragrances, flame retardants, antioxidants, odor-masking agents, antifogging agents and perfumes. Some cloths utilize microcapsules which may be ruptured to dispense a material.

More complex packages for dispensing a material are exemplified by a disposable swab having a rupturable container and a foam applicator in combination and a scrub sponge having a closed chamber which includes a closed, puncturable chamber containing a liquid scrub agent and a puncture member. Another puncturable package is employed in a disposable liquid applicator for the cleaning and waxing of floors and other surfaces. Other containers are utilized for dispensing a vapor from a volatile liquid.

A variety of laundry-related containers have been devised. These include containers for dispensing hydrogen peroxide into a clothes dryer for the bleaching of textiles, introducing detergent into a washer, and introducing detergent into a washer and fabric softener into a dryer by means of a single container.

Notwithstanding the creativity applied in the past to the dispensing of materials, there still is a need for improvements. For example, there is a need for a dispensing container which will permit application of a fluid without excessive waste or getting fluid on the hands.

SUMMARY OF THE INVENTION

The present invention addresses some of the difficulties and problems discussed above by providing a pull-activated container adapted to hold a fluid, volatile solid, or absorbent for a fluid wherein at least a portion of the container includes a laminate which, in turn, includes a first layer, a second layer, a third layer, and a grasping means. The first layer is a fibrous sheet, the second layer is a film having a first side and a second side, and the third layer is a porous fibrous sheet. The third layer is inside the container. The first layer is bonded to the first side of the second layer and has a first bonding strength and the third layer is bonded to the second side of the second layer and has a second bonding strength. For example, the first bonding strength may be greater than the second bonding strength to an extent sufficient to aid in selectively removing the first and second layers from the third layer without tearing the third layer. Finally, the grasping means is affixed to the first layer and has an affixation strength which is greater than the second bonding strength.

If desired, a portion of the first and second layers may be defined by lines of weakness sufficient to aid in removing such portion at least partially from the third layer. Desirably, the grasping means will be attached to the portion of the first layer which is defined by lines of weakness.

Desirably, the pull-activated container will include a liquid. For example, the container may include a gel, cream, or lotion.

DETAILED DESCRIPTION OF THE INVENTION

As used herein, the term "pull-activated container" means a container which is activated or opened by pulling on a portion or component of the container. That is, the contents of the container are made available, such as for dispensing, by pulling on a portion or component of the container. The term "fluid" is intended to include both gases and liquids, whereas the term "liquid" is meant to exclude gases.

The term "film" is used herein to mean a flat section of a thermoplastic polymer whose thickness is very thin in relation to its width and length.

The term "fibrous sheet" is used broadly herein to mean any sheet or web which is composed, at least in part, of fibers of any length. Thus, the sheet or web may be a woven or nonwoven sheet or web, all of which are readily prepared by methods well known to those having ordinary skill in the art. Moreover, the sheet or web may consist of a single layer or multiple layers. When multiple layers are present, only one needs to be fibrous. Thus, a multilayered fabric may include films, scrim, and other nonfibrous materials.

As used herein, the term "nonwoven web" means a web having a structure of individual fibers or threads which are interlaid, but not in an identifiable manner as in a knitted fabric. Nonwoven webs are readily prepared by known processes, such as meltblowing, coforming, spunbonding, air laying, wet laying, carding, and the like.

The term "cross-direction" is used herein to mean a direction which is the cross machine direction, i.e., a direction which is perpendicular to the direction of the motion of a fibrous sheet or film during its manufacture (the "machine direction").

The term "porous" in connection with a fibrous sheet means that the sheet is permeable to the fluid which is intended to pass out of or into the container. For example, when the container includes a liquid to be dispensed, a porous fibrous sheet will be a sheet through which the liquid present in the container may pass.

The pull-activated container of the present invention is adapted to hold a fluid, volatile solid, or absorbent for a fluid. In general, at least a portion of the container includes a laminate which, in turn, includes a first layer, a second layer, a third layer, and a grasping means.

Each of the first layer and the third layer is a fibrous sheet and each layer may be identical or different. The third layer must be porous, while the first layer may be porous. For example, each of the first and second layers may be a nonwoven web. As a further example, each of the first and third layers may be a nonwoven web prepared by such known processes as meltblowing, coforming, spunbonding, air laying, wet laying, and the like. As a practical matter, nonwoven webs prepared by meltblowing, coforming, and spunbonding are especially useful. By way of illustration only, such processes are exemplified by the following references, each of which is incorporated herein by reference:

(a) meltblowing references include, by way of example, U.S. Pat. No. 3,016,599 to R. W. Perry, Jr., U.S. Pat. No. 3,704,198 to J. S. Prentice, U.S. Pat. No. 3,755,527 to J. P. Keller et al., U.S. Pat. No. 3,849,241 to R. R. Butin et al., U.S. Pat. No. 3,978,185 to R. R. Butin et al., and U.S. Pat. No. 4,663,220 to T. J. Wisneski et al. See, also, V. A. Wente, "Superfine Thermoplastic Fibers", *Industrial and Engineering Chemistry*, Vol. 48, No. 8, pp. 1342-1346 (1956); V. A. Wente et al., "Manufacture of Superfine Organic Fibers", Navy Research Laboratory, Washington, D.C., NRL Report 4364 (111437), dated May 25, 1954, United States Department of Commerce, Office of Technical Services; and Robert R. Butin and Dwight T. Lohkamp, "Melt Blowing—A One-Step Web Process for New Nonwoven Products", *Journal of the Technical Association of the Pule and Paper Industry*, Vol. 56, No.4, pp. 74–77 (1973);

(b) coforming references include U.S. Pat. No. 4,100,324 to R. A. Anderson et al. and U.S. Pat. No. 4,118,531 to E. R. Hauser; and (c) spunbonding references include, among others, U.S. Pat. No. 3,341,394 to Kinney, U.S. Pat. No. 3,655,862 to Dorschner et al., U.S. Pat. No. 3,692,618 to Dorschner et al., U.S. Pat. No. 3,705,068 to Dobo et al., U.S. Pat. No. 3,802,817 to Matsuki et al., U.S. Pat. No. 3,853,651 to Porte, U.S. Pat. No. 4,064,605 to Akiyama et al., U.S. Pat. No. 4,091,140 to Harmon, U.S. Pat. No. 4,100,319 to Schwartz, U.S. Pat. No. 4,340,563 to Appel and Morman, U.S. Pat. No. 4,405,297 to Appel and Morman, U.S. Pat. No. 4,434,204 to Hartman et al., U.S. Pat. No. 4,627,811 to Greiser and Wagner, and U.S. Pat. No. 4,644,045 to Fowells.

The second layer is a film having a first side and a second side. The film may be impermeable to fluids, i.e., impermeable to both liquids and gases. If desired, the film layer may comprise two or more films bonded together by any known means. For example, a multilayered film may be prepared by coextruding two or more molten thermoplastic polymers or mixtures of polymers to form two or more layers. As another example, two or more preformed films may be bonded together by adhesives and/or heat in accordance with practices well-known to those having ordinary skill in the art.

The first layer is bonded to the first side of the second layer and the third layer is bonded to the second side of the second layer. Bonding may be accomplished by any known means. For example, either or both layers may be bonded to the second layer by adhesives. As another example, either or both layers may be laminated to the second layer by heat, such as by thermal point bonding (see, for example, U.S. Patent No. 3,855,046 to Hansen et al. and U.S. Pat. No. 4,493,868 to Meitner); in this instance, a bond pattern which does not result in significant thinning of the film is desired. A combination of adhesives and thermal point bonding may be employed. Another example of a bonding method is ultrasonic welding.

The bonding of the first layer to the first side of the second layer results in a first bonding strength therebetween.

As used herein, the term "bonding strength" simply refers to the strength of the bonding between any two layers or components. In the examples, bonding strength between layers was estimated by determining the average peel peak load substantially in accordance with ASTM D-2724.13 and Federal Test Method Standard No. 191A, Method 5951, utilizing a 2-inch by six-inch (about 5-cm by 15-cm) sample and a 1-inch (about 2.5-cm) gauge length. Similarly, the bonding of the third layer to the second side of the second layer results in a second bonding strength therebetween.

Finally, a grasping means is affixed to the first layer. While such grasping means may take any form, a tab most often will be employed. Because the tab may be affixed by means other than bonding as with an adhesive, such as by sewing, the tab is referred to as having an affixation strength. The third layer must be inside the container, with the first layer and the grasping means being located outside of the container.

In order to aid in selectively removing the first and second layers from the third layer, the first bonding strength may be greater than the second bonding strength. The extent of the difference in bonding strengths between the two layers need only be sufficient to accomplish the desired selective removal. That is, the relative strengths of the bonding of the two fibrous sheet layers to the film layer may be such that upon attempting to delaminate or peel the first layer from the second layer, the first layer and second layer remain bonded while the second layer delaminates from the third layer.

Alternatively, a portion of the first layer may contain lines of weakness sufficient to aid in removing such portion at least partially from the third layer. As used herein, the phrase "lines of weakness" means a weakening of the integrity or strength of a layer along one or more defined lines which permits the tearing or severing of the layer along such one or more defined lines. Thus, the term is intended to include both the singular and the plural. Such weakening may be accomplished by any means known to those having ordinary skill in the art, such as by partial cutting, thermal thinning, and the like. When the first layer is a meltblown, spunbonded, or similar nonwoven web, lines of weakness may be introduced during web formation by blocking selected orifices in the extrusion die.

If desired, lines of weakness also may be present in the second layer. When used, the lines of weakness in the second layer typically will correspond to or coincide with the lines of weakness in the first layer.

The number and lengths of the lines of weakness, which may be linear, curved, irregular, or any combination thereof, typically are matters of choice, depending upon the size of the opening desired. For example, a single line of weakness will result in a relatively small opening which may be particularly useful for dispensing small quantities of, for example, an ointment, cream, or lotion. The presence of two or more interconnected lines of weakness will result in a larger opening. Where three or more interconnected lines of weakness define, i.e., enclose, an area, such area may be completely removed from the container.

The container may be of any size and shape. For example, the container may be formed from two identical pieces of the laminate described above. Such pieces may be overlaid and sealed around the edges to define a volume or reservoir therebetween. Alternatively, one of the pieces may be the laminate described above and the other piece may be a film or other impervious material.

Most commonly, a fluid to be dispensed will be present in the pull-activated container of the present invention. For example, the fluid may be a liquid, such as a gel, cream, lotion, or solution. As examples of suitable liquids, the following may be mentioned by way of illustration only: hand and body lotions, cleansing creams, baby oil, disinfecting solutions, cleansing solutions, medicating gels, insect repellent solutions, sunscreen lotions and oils, tanning lotions and oils, shoe polishes, and the like.

A liquid need not be present in the container, however. Moreover, the movement of a fluid through the third layer upon activating the container need not be from inside the container to the outside. For example, a solid may be present in the container. By way of illustration, the solid may be an absorbent such as activated carbon or silica gel. In such case, the movement of fluid generally will be from outside the container to the inside, and the fluid typically will be a gas, such as water vapor or a malodorous gas or vapor. Alternatively, the solid present in the container may consist of a material which sublimes, such as naphthalene, in which case molecules of naphthalene vapor will move from inside the container to the outside.

The present invention is further described by the examples which follow. Such examples, however, are not to be construed as limiting in any way either the spirit or the scope of the present invention.

EXAMPLE 1

A three-layered laminate was prepared in which the first layer and the second layer were a spunbonded nonwoven web and the second layer was a three-layered film. The spunbonded nonwoven web was a 0.5 ounce per square yard or osy (about 17 grams per square meter or gsm) polypropylene spunbonded nonwoven web. The web was produced essentially as described in U.S. Pat. No. 3,802,817 to Matsuki and thermally point bonded, with a total bond area of about 15 percent, in accordance with U.S. Pat. No. 3,855,046 to Hansen et al.

The film consisted of three coextruded layers, designated herein as "A", "B", and "C". The layers constituted 30 percent, 40 percent, and 30 percent of the film, respectively, by weight, based on the total weight of the film. Layer B was sandwiched between layers A and C. The compositions of the three layers were as follows, with all percents being percents by weight, based on the weight of each layer:

Layer A 100 percent Catalloy® KS-084P (Himont Chemical Company, Wilmington, Del.).

Layer B 20 percent Catalloy® KS-084P;

29 percent Escorene® 3445 polypropylene (Exxon Chemical Americas, Houston, Tex.);

7 percent NA 334 low density polyethylene (Quantum Chemical Company); and 44 percent Ampacet 110310 titanium dioxide, which consists of 50 percent by weight titanium dioxide in polyethylene.

Layer C 20 percent Catalloy® KS-084P;

68 percent Escorene® 3445 polypropylene;

7 percent NA 334 low density polyethylene; and 5 percent Ampacet 110310 titanium dioxide.

The two spunbonded nonwoven webs were bonded to the three-layered film, one on each side, by thermal point bonding while the film was being stretched approximately 60 to 65 percent in the machine direction as described in Published European Patent Application No. EP 0 604 731 A1, which is incorporated herein by reference. The stretching of the film resulted in a reduction in film thickness from 0.6 mil (about 15 micrometers) to 0.4 mil (about 10 micrometers). The first layer of the resulting laminate was the spunbonded nonwoven web bonded to layer A of the second layer and the third layer of the resulting laminate was the spunbonded nonwoven web bonded to layer C of the second layer. A quilted baby objects bonding pattern having a bond area of about 17 percent was employed; see U.S. Pat. No. Des. 356,688.

The bonding strengths of the first and third layers were estimated by measuring average peel peak load. The average peel peak load for the first layer was 131±58 g and the average peel peak load for the third layer was 68 ±28 g.

A tab of the laminate was glued onto the first layer with an Arrow trigger-feed glue gun and an AP-10 all-purpose clear hot melt glue stick (Arrow Fastener Company, Inc., City?, New Jersey). Upon pulling on the tab, the first layer and second layer delaminated from the third layer.

A pouch was made by placing two 2-inch by 2-inch (about 5-cm by 5-cm) pieces of the laminate together, third sides facing each other. A tab as described above was glued to the first layer of one of the pieces. Three of the edges were thermally bonded or sealed with a Vertrod Thermal Impulse Heat Sealer (Model 14P, Vertrod Corporation), using a 2.8 dwell setting and a 3.9 temperature setting, to form a pouch open along one edge. Two ml of OFF! Skintastic® Insect Repellent (S. C. Johnson Wax, Racine, Wis.) was introduced into the pouch through the open edge which then was thermally sealed as just described. The pouch was stored at ambient temperature (about 20°–25° C.) for several days. The tab then was pulled to remove the first and second layer from the third area in the area of the tab. The insect repellent wetted through the exposed third layer and, when wiped on the skin, gave a controlled transfer of repellent to the skin.

EXAMPLE 2

Two pieces of the laminate employed in Example 1 were laid on top of each other with the third layers facing each other. Each piece was 2 inches (cross direction) by 10 inches (machine direction) (about 5 cm by 25.4 cm). The pieces were sealed to each other as described in Example 1 along one of the longer sides and both of the shorter sides to form a pouch having one open side. Two additional heat seals were made 2 inches (about 5 cm) from each other close to the center of the pouch. Each seal was normal to the long sides and extended across the width of the pouch, thereby forming a smaller, approximately 2-inch (about 5-cm) square pouch in the center of the original pouch. A tab was affixed with the hot glue gun as described in Example 1, with the glue line running normal to the longer side of the original pouch and within the smaller pouch. Approximately 1 g of black shoe cream (Kiwi Brands Inc., Pennsylvania) was placed in the smaller pouch and the remaining open side was sealed. The tab was pulled to expose the inner, third layer. When the exposed layer was wiped over a shoe, the shoe cream was transferred to the shoe and spread out in a thin layer. The tab was replaced over the exposed third layer and the reverse side of the pouch was used to polish the shoe.

EXAMPLE 3

A pouch as described in Example 1 was filled with 1 ml of a natural wax dispersion (Kiwi Elite Neutral Self-Shining Shoe Polish, Kiwi Brands Inc.). The tab was pulled and the dispersion was wiped onto a shoe without any smearing of wax onto the hand of the user.

EXAMPLE 4

Pouches were prepared as described in Example 1, except that a different film was employed and the film was not stretched when the spunbonded nonwoven webs were bonded to it. The film again consisted of three coextruded layers, designated herein as "D", "E", and "F". The layers constituted 10 percent, 80 percent, and 10 percent of the film, respectively, by weight, based on the total weight of the film. Layer E was sandwiched between layers D and F. The compositions of the three layers were as follows, with all percents being percents by weight, based on the weight of each layer:

Layer D 85 percent Catalloy® KS-084P;

10 percent Escorene® 3445 polypropylene; and 5 percent NA 334 low density polyethylene.

Layer E 40 percent Catalloy® KS-084P;

43 percent Escorene® 3445 polypropylene;

17 percent SCC 13602 high opacity titanium dioxide, 70/30 in low density polyethylene.

Layer F 35 percent Catalloy® KS-084P;

60 percent Escorene® 3445 polypropylene; and 5 percent NA 334 low density polyethylene.

The first layer of the resulting laminate was the spunbonded nonwoven web bonded to layer D of the second layer and the third layer of the resulting laminate was the spunbonded nonwoven web bonded to layer F of the second layer. Bonding of the three layers together was accomplished with thermal point bonding with a C-Star bonding pattern having a bond area of about 17 percent; the pattern has a cross-directional bar design interrupted by shooting stars. The bonding strengths in the machine direction of the first and third layers, measured as described in Example 1, were 109 g for the first layer and 120 g for the third layer.

Two variations were employed in the preparation of the pouches. For some pouches, third layers were placed together and for others, first layers were placed together. Tabs were affixed to the pouches with the Arrow glue gun as described in Example 1, except that the adhesive employed was Findakly Hot Melt Adhesive H2525A, a standard adhesive used to bond polyolefins which had been melted and shaped into rods to fit the glue gun. Depending on the variation, the tab was affixed to either the first layer or the third layer.

Pouches were filled separately with the insect repellent employed in Example 1, the shoe cream used in Example 2, the wax dispersion used in Example 3, a skin lotion (Jergens Advanced Therapy Lotion, The Andrew Jergens Company, Ohio), an aqueous detergent solution (diluted Palmolive Brand), and ethanol. Pulling the tab removed the outer layer and the film or second layer, allowing for controlled dispensing of the pouch contents to a desired surface. Both variations of pouches worked equally well, suggesting that the adhesive was bonding the tab through the outer nonwoven web layer directly to the film layer.

While the specification has been described in detail with respect to specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A pull-activated container adapted to hold a fluid, volatile solid, or absorbent for a fluid wherein at least a portion of the container comprises a laminate comprising a first layer, a second layer, a third layer, and a grasping means, in which:

the first layer is a fibrous sheet;

the second layer is a film having a first side and a second side;

the third layer is a fibrous sheet; and the third layer is inside the container;

wherein:

the first layer is bonded to the first side of the second layer and has a first bonding strength;

the third layer is bonded to the second side of the second layer and has a second bonding strength which is such that the second layer may be removed from the third layer without tearing the third layer; and the grasping means is affixed to the first or second layer and has an affixation strength which is greater than the second bonding strength.

2. The pull-activated container of claim 1, in which the first bonding strength is greater than the second bonding strength to an extent sufficient to permit selectively removing the first and second layers from the third layer.

3. The pull-activated container of claim 1, in which a portion of the first layer is defined by lines of weakness sufficient to aid in removing such portion at least partially from the third layer.

4. The pull-activated container of claim 3, in which the grasping means is affixed to the portion of the first layer which is defined by lines of weakness.

5. The pull-activated container of claim 1, in which the first layer is a nonwoven web.

6. The pull-activated container of claim 1, in which the nonwoven web is a spunbonded nonwoven web.

7. The pull-activated container of claim 1, in which the second layer is a nonwoven web.

8. The pull-activated container of claim 7, in which the nonwoven web is a spunbonded nonwoven web.

9. The pull-activated container of claim 1, in which the container contains liquid.

10. The pull-activated container of claim 9, in which the liquid is selected from the group consisting of a gel, cream, and lotion.

11. The pull-activated container of claim 1, in which the second layer is a multilayered film.

12. The pull-activated container of claim 11, in which the multilayered film is a three-layered film.

* * * * *